(12) United States Patent
Zaidel et al.

(10) Patent No.: US 9,140,708 B2
(45) Date of Patent: Sep. 22, 2015

(54) DIAGNOSTIC METHODS

(75) Inventors: Lynette Zaidel, Cranford, NJ (US); Steven Miller, Skillman, NJ (US); Guy Carpenter, London (GB); Gordon Proctor, London (GB); David Bartlett, London (GB); Rebecca Moazzez, London (GB)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/366,653

(22) PCT Filed: Dec. 20, 2011

(86) PCT No.: PCT/US2011/066078
§ 371 (c)(1),
(2), (4) Date: Jun. 18, 2014

(87) PCT Pub. No.: WO2013/095367
PCT Pub. Date: Jun. 27, 2013

(65) Prior Publication Data
US 2014/0348762 A1    Nov. 27, 2014

(51) Int. Cl.
*G01N 33/53*    (2006.01)
*A61K 8/00*    (2006.01)
*G01N 33/68*    (2006.01)
*C07K 16/18*    (2006.01)
*C07K 16/40*    (2006.01)

(52) U.S. Cl.
CPC ............ *G01N 33/6893* (2013.01); *C07K 16/18* (2013.01); *C07K 16/40* (2013.01); *G01N 2333/4721* (2013.01); *G01N 2333/4725* (2013.01); *G01N 2333/988* (2013.01); *G01N 2800/18* (2013.01)

(58) Field of Classification Search
None
See application file for complete search history.

(56) References Cited

U.S. PATENT DOCUMENTS 7,387,774 B2 *  6/2008  Faller et al. ............... 424/57
8,129,329 B2   3/2012  Fine et al.
8,513,182 B2   8/2013  Fine et al.

OTHER PUBLICATIONS

Banderas-Tarabay et al (Archives of Medicinal Research 33:499-505, 2002).*
Thornton et al (Glycobiology, 9(3):293-302, 1999).*
Wikstrom et al (Oral Microbiol Immunol, 16:345-352, 2001).*
Silva et al (Archives of Oral Biology, 54:86-90, 2009).*
Cheaib Z et al: "Impact of acquired enamel pellicle modification on initial dental erosion." Caries Research 2011 LNKD—PUBMED: 21412002, vol. 45, No. 2, Mar. 27, 2011, pp. 107-112, XP009162317, ISSN:1421-976X figure 1 CH.
Niedermeier et al, Impact of Saliva on Dental Erosions, IADR General Session, Mar. 19, 2011, downloaded from the Internet http://iadr.confex.com/iadr/2011sandiego/webprogram/paper147459, 1 page.
International Search Report and the Written Opinion issued in International Application PCT/US2011/66078 mailed Sep. 19, 2012. WO.
Jager D H J et al: "Effect of salivary factors on the susceptibility of hydroxyapatite to early erosion.", Caries Research 2011 LNKD—PUBMED :21997255, vol. 45, No. 6, Oct. 13, 2011, pp. 532-537, XP009162191, ISSN:1421-976X tables 1,2 NE.
Johansson Ann-Katrin et al: "Comparison of factors potentially related to the occurrence of dental erosion in high—and low-erosion groups", European Journal of Oral Sciences, vol. 110, No. 3 Jun. 2002, pp. 204-211, XP002682524, ISSN: 0909-8836 p. 208, right-hand column, paragraph 2; table 2 SW.
Li J et al: "Statherin is an in vivo pellicle constituent: identification and immune-quantification"Archives of Oral Biology, vol. 49, No. 5, May 2004, pp. 379-385, XP002682523, ISSN: 0003-9969 table 1 US.
Lussi et al., The role of diet in the aetiology of dental erosion, Caries Res. 2004;38 Suppl 1:34-44.
Piangprach et al., The Effect of Salivary Factors on Dental Erosion in Various Age Groups and Tooth Surfaces, J. American Dental Assoc., 140 2009 1137-1143. Downloaded from the internet at http://jada.ada.org/content/140/9/1137.long.
Written Opinion of the International Preliminary Examining Authority issued in International Application PCT/US2011/66078 mailed Dec. 4, 2013. WO.

* cited by examiner

*Primary Examiner* — Patricia A Duffy

(57) ABSTRACT

Described herein are methods for identifying a mammal having a heightened susceptibility to enamel erosion, together with kits therefor and uses and methods related thereto.

7 Claims, No Drawings

DIAGNOSTIC METHODS

CROSS-REFERENCE TO RELATED PATENT APPLICATIONS

The present application is a U.S. national stage entry under 35 U.S.C. §371 of Patent Cooperation Treaty Patent Application No. PCT/US2011/66078, filed Dec. 20, 2011, the entirety of which is incorporated herein by reference.

BACKGROUND

As awareness of erosion and the impact thereof increases among dental practitioners and patients, there is a need for approaches to correctly diagnose the source of erosion and identify individuals with heighted susceptibility to erosion. Unlike caries, which produce deep localized subsurface lesions due to prolonged exposure to bacterial acids, erosion results from dissolution and softening of the entire enamel surface from short and frequent exposures to low pH dietary acids, leading to softening and micron-scale mineral loss especially when followed by brushing with abrasive toothpastes. Dietary acids like citric acid are particularly damaging due to not only their acidic pH, but also their calcium-chelating capacity, which drives further enamel dissolution.

The acquired enamel pellicle (AEP) naturally provides some protection against acid attack on enamel. The AEP contains calcium and phosphate ions as well as proteins and enzymes. Pellicle formation is a complex, multi-step process in which precursor proteins like statherin and proline-rich proteins bind initially and provide binding sites for additional proteins (mucins, etc). Maturation involves cross-linking and dephosphorylation of pellicle proteins and binding of plaque bacteria in later stages after 2 hours. The composition of the pellicle is highly dependent on saliva content which varies with flow rate, stimulation, time of day, diet, etc. Salivary flow rate greatly impacts saliva pH, ionic components and buffering capacity.

Erosion can result from several conditions—frequent exposure to dietary acids, gastric acids or lack of sufficient saliva (xerostomia). Patients suffering from gastric erosion are normally identified through assessment of the severity and location of the erosive damage (upper palatal surfaces), while those with xerostomia are identified by visual inspection of the saliva and measurement of salivary flow rates. There is a link between erosion and increased intake of acidic drinks, lower salivary flow rate and lower salivary pH/buffer capacity resulting from the lower salivary flow rates. However, some patients with normal salivary flow rates and no signs of gastric acid exposure still suffer from dietary erosive damage, even when exposure to dietary acids is minimized, suggesting a heightened susceptibility to erosion, potentially related to their AEP. There is a need for a simple and reliable method to identify this subset of highly susceptible patients for proper treatment, as well as to identify patients for clinical studies evaluating the effects of oral care actives to reduce, mitigate and control dental erosion from dietary acids.

SUMMARY

It has been surprisingly found that patients with high susceptibility to dietary enamel erosion show 1) significantly lower mucin 5B, carbonic anhydrase 6, and/or higher statherin protein levels in whole mouth saliva, and 2) significantly lower total protein, statherin and/or calcium concentrations in AEP compared to a healthy control group with similar salivary flow rates and diet. These factors can be used to identify patients with susceptibility to erosion using a salivary and pellicle diagnostic method based on total protein concentration, calcium analysis and protein identification. As the test samples are saliva and salivary pellicle, sample collection is easy and there is abundant information related to protein and mineral content.

Accordingly, some embodiments of the present invention provide a method for identifying a patient having a heightened susceptibility to enamel erosion, comprising one or both of the following steps:
  (i) obtaining a sample of whole mouth saliva from the patient and measuring one or more of mucin 5B, carbonic anhydrase 6, and statherin protein levels in the saliva, wherein lower mucin 5B, lower carbonic anhydrase, and/or higher statherin protein levels relative to a control value each indicate a heightened susceptibility to enamel erosion; and
  (ii) obtaining a sample of acquired enamel pellicle (AEP) from the patient and measuring one or more of total protein, statherin and calcium concentrations in the AEP, wherein lower levels of each of these agents relative to a control value each indicate a heightened susceptibility to enamel erosion.

In some embodiments, the erosion is of dietary etiology.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the scope of the invention, its application, or uses.

Some embodiments of the present invention thus provide a method (Method 1) for identifying a patient having a heightened susceptibility to enamel erosion, comprising measuring one or more, for example any 2, 3, 4, or 5, e.g., all six, of the following:
  (i) measuring mucin 5B concentration in a sample of whole mouth saliva, e.g., unstimulated whole mouth saliva (UWMS), from the patient, wherein a lower mucin 5B concentration relative to a control value indicates a heightened susceptibility to enamel erosion;
  (ii) measuring carbonic anhydrase 6 concentration in a sample of whole mouth saliva e.g., unstimulated whole mouth saliva (UWMS), from the patient, wherein a lower carbonic anhydrase 6 concentration relative to a control value indicates a heightened susceptibility to enamel erosion;
  (iii) measuring statherin concentration in a sample of whole mouth saliva e.g., unstimulated whole mouth saliva (UWMS), from the patient, wherein a higher statherin concentration relative to a control value indicates a heightened susceptibility to enamel erosion;
  (iv) measuring total protein concentration in a sample of acquired enamel pellicle (AEP) from the patient, wherein a lower concentration of total protein relative to a control value indicates a heightened susceptibility to enamel erosion;
  (v) measuring statherin concentration in a sample of acquired enamel pellicle (AEP) from the patient, wherein a lower concentration of statherin relative to a control value indicates a heightened susceptibility to enamel erosion; and (vi) measuring calcium concentration in a sample of acquired enamel pellicle (AEP) from the patient, wherein a lower concentration of calcium relative to a control value indicates a heightened susceptibility to enamel erosion.

For example, the invention provides 1.1. Method 1 wherein the patient does not eat or drink for at least one hour, e.g., at least two hours prior to collection of samples.

1.2. Method 1 or 1.1 wherein a patient is identified as having heightened susceptibility to enamel erosion when the patient exhibits one or more of the following criteria:

| Parameter | Range indicating susceptibility to erosion |
| --- | --- |
| Mucin 5B (UWMS) | <250 µg/ml |
| Carbonic anhydrase 6 (UWMS) | <35 µg/ml |
| Statherin (UWMS) | >15 µg/ml |
| AEP 1 hour statherin | <30 ng |
| AEP 1 hour calcium | <0.001 mmol/mm$^2$ |

1.3. Method 1.2 wherein the patient identified as having heightened susceptibility to enamel erosion meets at least two of the criteria identified in Method 1.2.

1.4. Any of the foregoing Methods comprising measuring mucin 5B, carbonic anhydrase and statherin in whole mouth saliva.

1.5. Any of the foregoing methods wherein the patient's AEP is sampled by placing in the patient's mouth hydroxyapatite or enamel blocks mounted in a palatal mouth tray/splint worn for 0.5-2 hours, e.g., about 1 hour, and collecting AEP from the blocks after removal from the patient's mouth.

1.6. Any of the foregoing methods further comprising treating a patient identified as having heightened susceptibility to enamel erosion comprising administering or directing the patient to administer an effective therapeutic agent or product to the teeth for the control of enamel or dentin erosion including one or more of the following:
  (a) a fluoride treatment selected from fluoride mouth rinse and high fluoride concentration toothpaste;
  (b) a toothpaste comprising calcium phosphate or calcium abrasives such as calcium pyrophosphate, dicalcium phosphate dihydrate or calcium carbonate; (c) an oral care product, e.g., a mouthwash or dentifrice comprising L-arginine, in free or salt form;
  (d) a dentin bonding agent or varnish to areas of exposed dentin;
  (e) an oral care product containing stannous ions
  (f) an oral care product containing calcium ions Some embodiments of the present invention further provide a kit for diagnosing heightened susceptibility to enamel erosion comprising means for measuring concentrations of one or more of the following proteins mucin 5B, carbonic anhydrase 6, and statherin, e.g., comprising antibodies to said proteins, together with instructions for use.

The invention further provides the use of antibodies to one or more of mucin 5B, carbonic anhydrase 6, and statherin in the manufacture of a kit for diagnosing heightened susceptibility to enamel erosion.

In some embodiments, the present invention provides methods for identifying a mammal having a heightened susceptibility to enamel erosion, comprising: a. obtaining a sample of whole mouth saliva from the oral cavity of the mammal; b. measuring the concentration of one or more of the following biomarkers: i) mucin 5B; ii) carbonic anhydrase 6; and iii) statherin; and comparing the mucin B concentration; the carbonic anhydrase 6 concentration; and/or statherin concentration to a control value for each of the biomarkers; wherein the control value is the concentration of the biomarker in a whole mouth saliva sample taken from the oral cavity of a mammal not suffering from erosion of the enamel; and wherein a lower mucin 5B concentration relative to the control value for mucin 5B indicates a heightened susceptibility to enamel erosion; wherein a lower carbonic anhydrase 6 concentration relative to the control value for carbonic anhydrase 6 indicates a heightened susceptibility to enamel erosion; and wherein a higher statherin concentration relative to the control value for statherin indicates a heightened susceptibility to enamel erosion. In some embodiments, the enamel erosion is of dietary etiology.

In some embodiments, the whole mouth saliva is unstimulated whole mouth saliva. In some embodiments, the whole mouth saliva is stimulated.

In some embodiments, the mammal is identified as having heightened susceptibility to enamel erosion when the mammal exhibits one or more of the following criteria:

| Parameter | Range indicating susceptibility to erosion |
| --- | --- |
| Mucin 5B (UWMS) | <250 µg/ml |
| Carbonic anhydrase 6 (UWMS) | <35 µg/ml |
| Statherin (UWMS) | >15 µg/ml |

In some embodiments, the mammal is identified as having heightened susceptibility to enamel erosion on the basis of exhibiting at least two of the following criteria:

| Parameter | Range indicating susceptibility to erosion |
| --- | --- |
| Mucin 5B (UWMS) | <250 µg/ml |
| Carbonic anhydrase 6 (UWMS) | <35 µg/ml |
| Statherin (UWMS) | >15 µg/ml |

Some embodiments of the present invention provide methods which further comprise the step of treating the mammal identified as having heightened susceptibility to enamel erosion, wherein the step comprises administering to the oral cavity of said mammal an effective amount of an agent or product that prevents or reduces dentin or enamel erosion.

In some embodiments, the agent or product that prevents or reduces dentin or enamel erosion is selected from: a fluoride mouth rinse; a high fluoride concentration toothpaste; a toothpaste comprising calcium phosphate or calcium abrasives such as calcium pyrophosphate, dicalcium phosphate dihydrate or calcium carbonate; an oral care composition comprising L-arginine, in free or salt form; a dentin bonding agent or varnish; an oral care composition comprising a stannous ion source; and a combination of two or more thereof.

Some embodiments provide a kit for diagnosing a heightened susceptibility to enamel erosion in a mammal comprising means for measuring concentrations of one or more of mucin 5B, carbonic anhydrase 6, and statherin in a whole mouth saliva sample taken from the oral cavity of a mammal, together with instructions for use.

In some embodiments, the mammal is selected from a human; a feline; and a canine. In some embodiments, the mammal is a human.

Some embodiments of the present invention provide for the use of antibodies to one or more of mucin 5B, carbonic anhydrase 6, and statherin in the manufacture of a kit for diagnosing heightened susceptibility to enamel erosion in a mammal.

Other embodiments of the present invention provide a method for identifying a mammal having a heightened susceptibility to enamel erosion, comprising: a. obtaining a sample of acquired enamel pellicle (AEP) from the oral cavity of a mammal; b. measuring the concentration of one or more of the following biomarkers: i) total protein; ii) statherin; and iii) calcium; and comparing the total protein concentration; the statherin concentration; and/or the calcium concentration to a control value for each of the biomarkers; wherein the control value is the concentration of the biomarker in an AEP sample taken from the oral cavity of a mammal not suffering from erosion; and wherein a lower concentration of total protein relative to the control value for total protein indicates a heightened susceptibility to enamel erosion; wherein a lower concentration of statherin relative to the control value for statherin indicates a heightened susceptibility to enamel erosion; and wherein a lower concentration of calcium relative to the control value for calcium indicates a heightened susceptibility to enamel erosion.

In some embodiments, the mammal is identified as having heightened susceptibility to enamel erosion when the mammal exhibits one or both of the following criteria:

| Parameter | Range indicating susceptibility to erosion |
| --- | --- |
| AEP 1 hour statherin | <30 ng |
| AEP 1 hour calcium | <0.001 mmol/mm$^2$ |

Some embodiments provide a kit for diagnosing heightened susceptibility to erosion in a mammal comprising means for measuring calcium, statherin and/or total protein in a sample of AEP formed over 1 hour or more.

As used throughout, ranges are used as shorthand for describing each and every value that is within the range. Any value within the range can be selected as the terminus of the range. In addition, all references cited herein are hereby incorporated by referenced in their entireties.

In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLE

Example 1

A clinical trial is carried out to identify markers for susceptibility to enamel erosion. Enrollment criteria include (i) salivary flow rates >0.2 ml/min unstimulated, and (ii) no signs of gastric acid erosive damage or abnormal salivary function.

Two patient groups (n=30 each) are examined, one with no signs of dietary erosion ("Control") and the other with signs of dietary erosion ("Erosion"), both groups having similar diet and normal salivary flow rates. AEP is sampled by placing in the patient's mouth hydroxyapatite or enamel blocks mounted in a palatal mouth tray/splint worn for 1 hour, and collecting AEP from the blocks after removal from the patient's mouth AEP is also sampled from the patients' incisors.

Mucin 5b, Carbonic Anhydrase 6 and Statherin in Saliva:

The unstimulated whole mouth saliva (UWMS) is analyzed by immunoblotting for MUC 5b, carbonic anhydrase 6 and statherin. Semi-quantitative analysis is performed by comparing antibody staining intensity against purified MUC 5b, carbonic anhydrase 6 and statherin standards. There is approximately 25% less MUC 5b ($p<0.05$) and carbonic anhydrase 6 ($p<0.05$) in the whole saliva from erosion patients compared to controls. Conversely there is significantly more (approximately twice) statherin in the same samples ($p<0.001$).

Total Protein Content in AEP Formed Over 1 Hour In Situ:

Using the BCA assay, the total protein amount within AEP collected by Sialostrip papers is compared. There is no difference between controls and erosion patients in total protein within the AEP on the native upper incisors formed over >2 hours. In contrast, the AEP covering either hydroxyapatite or enamel blocks held within the splint for 1 hour did show significant differences ($p<0.01$ and $p<0.05$ respectively, n=18 in each group). This suggests a slower rate of AEP formation in the erosion group.

Statherin in AEP after 1 Hour of In Situ Exposure:

Analyses of specific proteins within the AEP reveals little difference in mucin or carbonic anhydrase 6 levels (although for many subjects no proteins can be detected) but there is a clear reduction for statherin.

Calcium in AEP after 1 Hour of In Situ Exposure:

Ion analysis (ICP/MS) of AEP which forms on a hydroxyapatite disk for 1 hour revealed significant amounts of calcium and phosphorus. Furthermore, the calcium level is significantly higher for the control vs. erosion group. Using the same elution technique, little calcium or phosphorus is eluted from non-saliva treated hydroxyapatite disks, suggesting the calcium and phosphorus was associated with absorbed salivary protein.

In summary, saliva and enamel pellicle samples are collected from large groups of healthy and erosion subjects. The use of human enamel or hydroxyapatite does not provide any contradictions and gives similar results in all assays used. The use of ICP/MS requires further elucidation although it has shown a difference between the two groups. Profilometry suggests a protective effect of pellicle and a difference between the groups. The increased susceptibility to erosion could be accounted for by reduced rate of pellicle formation. Although the difference in pellicle protein amounts is not detected from the subjects' own teeth (incisors) it is apparent on both enamel and hydroxyapatite blocks held in the splint. The rate of pellicle formation may depend on concentrations of pellicle constituents in saliva but may also be affected by microbial degradation or other ionic factors.

From the above examples, diagnostic methods are developed using any or all of the following parameters to identify an individual with heightened susceptibility to dental erosion, e.g.,

| Parameter | Range indicating susceptibility to erosion |
| --- | --- |
| Mucin 5B (UWMS) | <250 µg/ml |
| Carbonic anhydrase 6 (UWMS) | <35 µg/ml |

-continued

| Parameter | Range indicating susceptibility to erosion |
|---|---|
| Statherin (UWMS) | >15 µg/ml |
| AEP 1 hour statherin | <30 ng |
| AEP 1 hour calcium | <0.001 mol/mm$^2$ |

The invention claimed is:

1. A method of treating enamel erosion of dietary etiology in a mammal, comprising:
   identifying a mammal that is in need of treatment for dietary enamel erosion; and
   administering to the oral cavity of said mammal an effective amount of an agent or product that reduces dentin or enamel erosion;
   wherein:
   said identifying is performed by a process comprising the steps of:
   a. obtaining a sample of whole mouth saliva from the oral cavity of the mammal;
   b. measuring the concentration of one or more of the following biomarkers:
      i) mucin 5B;
      ii) carbonic anhydrase 6; and
      iii) statherin; and
   c. comparing the mucin B concentration; the carbonic anhydrase 6 concentration; and/or statherin concentration to a control value for each of said biomarkers;
   wherein said control value is the concentration of said biomarker in a whole mouth saliva sample taken from the oral cavity of a mammal not suffering from erosion; and
   wherein a lower mucin 5B concentration relative to said control value for mucin 5B indicates a heightened susceptibility to enamel erosion;
   wherein a lower carbonic anhydrase 6 concentration relative to said control value for carbonic anhydrase 6 indicates a heightened susceptibility to enamel erosion; and
   wherein a higher statherin concentration relative to a control value for statherin indicates a heightened susceptibility to enamel erosion.

2. The method of claim 1, wherein the whole mouth saliva is unstimulated whole mouth saliva.

3. The method of claim 1, wherein the mammal is identified as having heightened susceptibility to enamel erosion when the mammal exhibits one or more of the following criteria:

| Parameter | Range indicating susceptibility to erosion |
|---|---|
| Mucin 5B (UWMS) | <250 µg/ml |
| Carbonic anhydrase 6 (UWMS) | <35 µg/ml |
| Statherin (UWMS) | >15 µg/ml. |

4. The method of claim 1, wherein the mammal is identified as having heightened susceptibility to enamel erosion on the basis of exhibiting at least two of the following criteria:

| Parameter | Range indicating susceptibility to erosion |
|---|---|
| Mucin 5B (UWMS) | <250 µg/ml |
| Carbonic anhydrase 6 (UWMS) | <35 µg/ml |
| Statherin (UWMS) | >15 µg/ml. |

5. The method of claim 1, further comprising the step wherein the mammal is required to abstain from eating or drinking for at least 1 hour before the sample is taken from the oral cavity.

6. The method of claim 1, wherein the agent or product that reduces dentin or enamel erosion is selected from: a fluoride mouth rinse; a high fluoride concentration toothpaste; a toothpaste comprising calcium phosphate or calcium abrasives such as calcium pyrophosphate, dicalcium phosphate dihydrate or calcium carbonate; an oral care composition comprising L-arginine, in free or salt form; a dentin bonding agent or varnish; an oral care composition comprising a stannous ion source; and a combination of two or more thereof.

7. The method of claim 1, wherein the mammal is a human.

* * * * *